US011969494B2

(12) United States Patent
Duperray et al.

(10) Patent No.: US 11,969,494 B2
(45) Date of Patent: Apr. 30, 2024

(54) NON-THERAPEUTIC ORAL USE OF A COMPOSITION FOR WHITENING AND/OR LIGHTENING THE SKIN COMPRISING CYSTINE AND GLUTATHIONE IN A CYSTINE-GLUTATHIONE RATIO RANGING FROM 1.5 TO 4

(71) Applicant: BRETAGNE CHIMIE FINE, Pleucadeuc (FR)

(72) Inventors: Joel Duperray, Trefflean (FR); Renaud Sergheraert, Baden (FR)

(73) Assignee: BRETAGNE CHIMIE FINE, Pleucadeuc (FR)

( * ) Notice: Subject to any disclaimer, the term of this patent is extended or adjusted under 35 U.S.C. 154(b) by 26 days.

(21) Appl. No.: 17/427,369

(22) PCT Filed: Feb. 10, 2020

(86) PCT No.: PCT/EP2020/053311
§ 371 (c)(1),
(2) Date: Jul. 30, 2021

(87) PCT Pub. No.: WO2020/165084
PCT Pub. Date: Aug. 20, 2020

(65) Prior Publication Data
US 2022/0016005 A1 Jan. 20, 2022

(30) Foreign Application Priority Data
Feb. 11, 2019 (FR) ...................................... 1901355

(51) Int. Cl.
*A61K 8/44* (2006.01)
*A61K 8/64* (2006.01)
*A61Q 19/02* (2006.01)

(52) U.S. Cl.
CPC ............... *A61K 8/447* (2013.01); *A61K 8/64* (2013.01); *A61Q 19/02* (2013.01); *A61K 2800/5922* (2013.01); *A61K 2800/92* (2013.01)

(58) Field of Classification Search
None
See application file for complete search history.

(56) References Cited

U.S. PATENT DOCUMENTS

| 2009/0208434 A1* | 8/2009 | Schmaus | A61P 17/04 424/59 |
| 2011/0212201 A1* | 9/2011 | Rana | A61K 36/53 424/769 |
| 2013/0310457 A1* | 11/2013 | Ramesh | A61K 9/0056 514/560 |

FOREIGN PATENT DOCUMENTS

| CN | 103535721 A | 1/2014 |
| CN | 103892269 A | 7/2014 |
| JP | 2016-88875 A | 5/2016 |
| KR | 20120025175 A | 3/2012 |
| WO | 2007/116428 A2 | 10/2007 |
| WO | 2016/117762 A1 | 7/2016 |

OTHER PUBLICATIONS

English translation of KR 2012/0025175 (Mar. 15, 2012) (Year: 2012).*
Kawasaki et al., "Effect of Ingestion of Supplements Containing Cystine and Cysteine Peptide Yeast Extract on Skin of Japanese Women: a Double-blind Randomized Controlled Trial." Nippon Eiyo Shokuryo Gakkaishi; 2015; vol. 68, No. 4, pp. 157-163 with English Abstract.
Wang et al., "Beauty Product Pharmaceutics"; Liaoning Science and Technology Publishing House; Feb. 2012, 2 pages with English Abstract.
Wu., "Nutrition and Disease Prevention Canon: Dr. Wu on Disease Nursing"; China Medical Science Press; Jun. 2015, 3 pages with English Abstract.
Office Action dated Nov. 23, 2021, in connection with corresponding Chinese Application No. 202080012860.0 (12 pp., including machine-generated English translation).
International Search Report dated Apr. 24, 2020 in corresponding International application No. PCT/EP2020/053311; 4 pages.
International Preliminary Report on Patentability dated Oct. 30, 2020 in corresponding International application No. PCT/EP2020/053311; 9 pages.
Supplementary Search Report dated Jun. 1, 2022 in Chinese Patent Application No. 2020800128600 (with English translation); 8 pages.
"Melanin dosage and photos on reconstructed skin epidermis"; BCF Life Sciences; Marot & Cie, Vannes; Dec. 2019; 2 pages.
Boo., "Metabolic Basis and Clinical Evidence for Skin Lightening Effects of Thiol Compounds"; Antioxidants; Mar. 4, 2022; vol. 11, No. 503, 20 pages.
Duperray et al., "The effects of the oral supplementation of L-Cystine associated with reduced L-Glutathione-GSH on human skin pigmentation: a randomized, double-blinded, benchmark- and placebo-controlled clinical trial"; Journal of Cosmetic Dermatology; Mar. 29, 2021; 12 pages.

* cited by examiner

*Primary Examiner* — David J Blanchard
*Assistant Examiner* — Sarah J Chickos
(74) *Attorney, Agent, or Firm* — Maier & Maier, PLLC

(57) ABSTRACT

The non-therapeutic, cosmetic, oral use of a composition as an active ingredient for whitening and/or lightening the skin and/or depigmenting the skin, in particular for reducing the size of brown spots, including at least cystine and glutathione in a cystine/glutathione ratio ranging from 1.5 to 4, the composition advantageously further comprising glycine and/or glutamine Preferably, the composition also includes at least one component selected from the group formed by zinc or one of its salts, copper or one of its salts, selenium or one of its salts, vitamins B, in particular B3, B5, B6 and/or B8, vitamin E, melon juice extracts, horsetail extracts and mixtures of these components.

12 Claims, No Drawings

NON-THERAPEUTIC ORAL USE OF A COMPOSITION FOR WHITENING AND/OR LIGHTENING THE SKIN COMPRISING CYSTINE AND GLUTATHIONE IN A CYSTINE-GLUTATHIONE RATIO RANGING FROM 1.5 TO 4

FIELD

The present invention relates to the field of orally administered cosmetic compositions having a skin whitening and/or lightening and/or depigmenting action.

BACKGROUND

For several years now, there has been a clear increase in consumer demand for skin whitening and/or lightening compositions.

In Asia, the use of this type of product is very common because the search for a clear skin is an ancient and still highly sought after aesthetic criterion. More generally, at different times in their lives, some people see darker spots appear on their skin, particularly on the face and hands, which generate areas of non-homogenous appearance.

These spots are generally due to a high concentration of melanin in the keratinocytes located on the surface of the skin. In fact, biological melanin is the pigment responsible for the colouring of the skin, it is made up of eumelanin and pheomelanin formed in the melanocytes of the basal layer of the skin.

Eumelanin is the most common type of integumentary melanin, it is brown to black in colour. Its presence in important quantity gives to the teguments, in particular to the skin, a dark brown or black colour, its power of protection against the damage caused to the epidermis by the UV rays is total. Eumelanin is formed from a mixture of 5,6-dihydroxy-indole-2-carboxylic acid (DHICA) and 5,6-dihydroxyindole (DHI) macromolecules.

The mechanism of eumelanin formation is particularly complex and involves the following main steps:

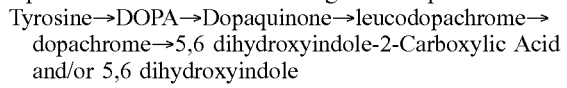
Tyrosine→DOPA→Dopaquinone→leucodopachrome→dopachrome→5,6 dihydroxyindole-2-Carboxylic Acid and/or 5,6 dihydroxyindole Tyrosinase (monophenol dihydroxyl phenylalanine: oxygen oxido-reductase EC 1.14.18.1) is the essential enzyme involved in this sequence of reactions. In particular, it catalyses the transformation of tyrosine into Dopa (dihydroxyphenylalanine) through its hydroxylase activity and the transformation of Dopa into Dopaquinone through its oxidase activity.

Pheomelanin is lighter in colour than eumelanin, its colour is yellow to red. Pheomelanin is also formed from a mixture of macromolecules synthesized in the melanocytes from tyrosine. In the presence of intracellular cysteine, a certain amount of tyrosine is converted to cysteinyl dopa and then to a polymer whose main monomer contains benzothiazole and dihydroisoquinoline:

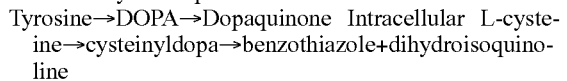
Tyrosine→DOPA→Dopaquinone Intracellular L-cysteine→cysteinyldopa→benzothiazole+dihydroisoquinoline There are already many products known for their whitening and/or depigmenting activity, such as hydroquinone, kojic acid, arbutin, glutathione and certain flavonoids.

Thus a substance is recognised as whitening or depigmenting if it acts directly on the vitality of the epidermal melanocytes where melanogenesis takes place, and/or if it interferes with one of the stages of melanin biosynthesis either by inhibiting one of the enzymes involved in melanogenesis or by intercalating as a structural analogue of one of the chemical compounds of the melanin synthesis chain, which chain can then be blocked and thus ensure depigmentation, and therefore lightening and/or whitening of the skin.

Some bleaching/depigmenting products are known to inhibit the tyrosinase enzyme, which leads to a decrease in the synthesis of pheomelanin and eumelanin. This reduction in the amount of eumelanin has a whitening/depigmenting effect, but it also contributes to a decrease in the skin's natural protective power against UV damage.

Glutathione is known for its high intracellular antioxidant power and is the first line of defence against free radicals. It is also known in the cosmetic industry for its topical skin whitening and/or lightening effects. However, when used orally, its bioavailability is controversial on the grounds that, in the absence of a specific vehicle at the cell membrane, it is susceptible to degradation by peptidases in the gastrointestinal tract.

Patent application WO2016/117762 A1 discloses the use of a composition, particularly for oral use, for whitening skin comprising gooseberry extract and glutathione.

In addition, patent application KR 2012 0025175 A describes a composition for improving skin tone or whitening skin comprising an extract of satsuma mandarin, cystine and vitamin C.

There is therefore still a need for new oral compositions with good depigmenting and/or whitening properties for lightening the whole face and/or body or for lightening and making more homogeneous more specific areas of the face and/or body. These compositions must also be stable, non-irritating, non-toxic and non-allergenic to the skin.

Surprisingly and advantageously, the authors of the present invention have succeeded in overcoming the problems of the prior art and have shown that the oral use of a composition comprising at least cystine and glutathione in a particular ratio makes it possible to obtain very satisfactory properties in terms of whitening, lightening, depigmentation of the skin and in particular for reducing the size of pigmentary brown spots.

Other aspects, advantages, properties of the present invention are presented in the following description and examples.

SUMMARY

The object of the present invention is the non-therapeutic, cosmetic, oral use of a composition as an active ingredient for whitening and/or lightening the skin and/or depigmenting the skin, in particular for reducing the size of brown spots, the said composition comprising at least cystine and glutathione in a cystine/glutathione ratio ranging from 1.5 to 4, preferably from 1.5 to 3, and preferably from 1.5 to 2.5 and advantageously from 1.8 to 2.2.

It is also aimed at a non-therapeutic, cosmetic method for whitening and/or lightening and/or depigmenting the skin, comprising a step of administering to an individual orally a composition comprising at least cystine and glutathione in a cystine/glutathione ratio ranging from 1.5 to 4, preferably from 1.5 to 3, and preferably from 1.5 to 2.5 and advantageously from 1.8 to 2.2.

An advantage of the composition according to the present invention is that it has very satisfactory skin whitening and/or lightening and/or depigmentation properties and in particular a reduction in the size of brown pigment spots.

In this text, the expressions "bleaching", "lightening" and "depigmentation" used to define the properties of the compositions according to the invention have the same meaning, as do the expressions "bleaching", "lightening" and "depigmenting". In particular, these expressions do not refer to a process involving the inhibition of an enzyme leading to the prevention of all melanin formation. Indeed, the composition according to the invention also has the advantage of partly guaranteeing the natural protective power of the skin against damage caused by UV rays.

"Skin" means the skin of the face and/or body, preferably the face.

Without wishing to be bound to any theory, it appears that the composition according to the invention having a precise cystine/glutathione ratio makes it possible to significantly increase the intracellular cysteine concentration and to maintain an intracellular cysteine/glutathione level, it also makes it possible to direct the melanin synthesis pathway towards an increase in the production of pheomelanin and a decrease in the production of eumelanin. Consequently, in comparison with the substances of the prior art which have the effect of inhibiting the action of the tyrosinase enzyme and thus of inhibiting the formation of eumelanin and pheomelanin, the composition according to the invention still allows the synthesis of pheomelanin. Pheomelanin has a certain UV absorption capacity, even if it is less than that of eumelanin.

The composition according to the invention also has the advantages of conferring a more luminous, radiant and homogeneous skin, in particular a clearer complexion, a fresher, more rested appearance, that is a "healthy glow" effect.

It also promotes the renewal of the keratinocytes that make up the cells of the epidermis, the surface layer of the skin.

The composition according to the invention makes it possible to attenuate or even treat a blurred, dull, heterogeneous skin complexion and more particularly to treat dyschromia and to reduce the size of brown spots.

The composition according to the invention is administered orally, allowing an effective and lasting whitening/lightening action on the whole of the skin.

DETAILED DESCRIPTION

The composition used according to the invention comprises cystine which is an amino acid composed of two cysteine monomers linked by a disulphide bridge.

Preferably, the cystine used is a very pure cystine in which the main impurities are in trace amounts, in particular the used cystine comprises less than 5 ppm of heavy metals, advantageously it comprises less than 5 ppm of heavy metals, less than 100 ppm of sulphates and less than 0.004% of ammonium. The determination of heavy metals is performed by colorimetry in the presence of thioacetamide (Ph. Eur. 9th Ed. 2.4.8, limit test D), the determination of sulphates is carried out in the presence of barium salts, in an acid medium (Ph. Eur. 9eme Ed 2.4.13), the determination of ammonium is carried out by ion exchange chromatography with post-column derivatisation with ninhydrin (Ph. Eur. 9th Ed 2.2.56). Preferably the cystine used in the present invention is the cystine marketed under the name Traced L-Cystine by the company BCF Life Sciences.

Cystine is used in the composition according to the invention in the form of a free amino acid, advantageously the amount of cystine in said composition ranges from 30 to 60%, preferably from 35 to 45% by weight with respect to the total weight of said composition.

The composition used according to the invention also comprises glutathione. Glutathione is a pseudo-tripeptide formed by the condensation of glutamic acid, cysteine and glycine. Glutathione is used in the composition according to the invention in free form. In particular, the glutathione used in the present invention is glutathione as such, in peptide form, it is not in yeast form.

Indeed, in some applications where the use of glutathione is not allowed, yeast is used instead of glutathione. Yeast generally contains glutathione in an amount that cannot always be determined. Furthermore, the activity/efficiency of a given amount of yeast does not always correspond to the activity/efficiency of the same amount of free glutathione. Therefore, when yeast is used, it may be difficult to establish the cystine/glutathione ratio.

Advantageously, the glutathione used in the composition according to the present invention is in the reduced form known as "GSH" form.

Preferably, the amount of glutathione in the composition used according to the invention ranges from 10 to 30%, preferably from 15 to 25% by weight based on the total weight of said composition.

Advantageously, the composition used according to the invention comprises glutamine Glutamine is an amino acid used in the composition according to the invention in free form.

Preferably, glutamine is used in the composition according to the invention in a cystine/glutamine ratio ranging from 3.5 to 5.0, preferably ranging from 4.0 to 4.5.

Preferably, the amount of glutamine in the composition used according to the invention ranges from 3 to 20%, preferably from 5 to 15% by weight based on the total weight of said composition.

Advantageously, the composition used according to the invention comprises glycine. Glycine is an amino acid used in the composition according to the invention in free form.

Preferably, glycine is used in the composition according to the invention in a cystine/glycine ratio ranging from 7 to 9.5, preferably ranging from 8.0 to 8.5.

Preferably, the amount of glycine in the composition used according to the invention ranges from 1 to 10%, preferably from 2 to 8% by weight based on the total weight of said composition.

Advantageously, the composition used according to the invention comprises calcium ascorbate, also called "vitamin C".

Preferably, calcium ascorbate is used in the composition according to the invention in a cystine to calcium ascorbate ratio ranging from 3.5 to 5.5, preferably ranging from 4.0 to 5.0.

Preferably, the amount of calcium ascorbate in the composition used according to the invention ranges from 3 to 20%, preferably from 5 to 15% by weight based on the total weight of said composition.

The composition used according to the invention comprises at least one component selected from the group formed by zinc or one of its salts, copper or one of its salts, selenium or one of its salts, vitamins B, in particular B3, B5, B6 and/or B8, vitamin E, melon juice extracts and horsetail extracts, as well as mixtures of these components.

In general, for the purposes of this text, "salt" means any salt that is adequately safe.

The amount of vitamin B3 in the composition used according to the present invention ranges from 0.5 to 10%, preferably from 1 to 5% by weight based on the total weight of said composition.

Vitamin B3 (or vitamin PP) may be present in the food supplement in the form of one or more compounds such as nicotinamide (or niacinamide), nicotinic acid (or niacin), nicotinyl alcohol, and salts and derivatives thereof.

Derivatives include nicotinic acid esters such as, for example, tocopheryl nicotinate, nicotinic amino acids, carboxylic acid esters of nicotinic alcohol, nicotinic acid N-oxide and N-oxydeniacinamide.

The amount of vitamin B3 in the composition used according to the present invention ranges from 0.5 to 10%, preferably from 1 to 5% by weight based on the total weight of said composition.

Advantageously, the vitamin B3 content in the composition used corresponds to the maximum content authorized by the regulations in force.

Vitamin B5 is pantothenic acid. It may be present in the dietary supplement in the form of pantothenic acid or as a salt of this acid.

Preferably, calcium pantothenate is used in the composition according to the invention.

The amount of vitamin B5 in the composition used according to the present invention ranges from 0.05 to 5%, preferably from 0.5 to 3% by weight based on the total weight of said composition.

Advantageously, the vitamin B5 content of the composition used according to the invention corresponds to the maximum content authorized by the regulations in force.

Vitamin B6 may be present in the composition used according to the present invention in the form of one or more compounds such as pyridoxine, pyridoxic acid, pyridoxine esters such as pyridoxine tripalmitate, pyridoxine amines such as pyridoxamine, as well as their salts and derivatives.

As derivatives, we may mention the compounds selected from the group formed by pyridoxal and pyridoxal phosphate.

Preferably, pyridoxine hydrochloride is used in the composition used according to the present invention.

The amount of vitamin B6 in the composition used according to the present invention ranges from 0.01 to 5%, preferably from 0.05 to 1% by weight with respect to the total weight of said composition Advantageously, the vitamin B6 content in the composition used according to the present invention corresponds to the maximum content authorized by the regulations in force.

The amount of vitamin B8 in the composition used according to the present invention ranges from 0.001 to 0.5%, preferably from 0.005 to 0.1% by weight based on the total weight of said composition.

Advantageously, the vitamin B8 content in the composition used according to the present invention corresponds to the maximum content authorized by the regulations in force.

Of course, the salts used in the formulation of the composition used according to the present invention are selected for their safety. Examples include zinc, copper and selenium salts in chelated forms with amino acids.

The amount of zinc in the composition used according to the present invention ranges from 0.1 to 2%, preferably from 0.5 to 1.2% by weight based on the total weight of said composition.

Advantageously, the zinc content in the composition corresponds to the maximum content authorized by the regulations in force.

The amount of copper in the composition used according to the present invention ranges from 0.01 to 1%, preferably from 0.05 to 0.5% by weight with respect to the total weight of said composition Advantageously, the copper content in the composition corresponds to the maximum content authorized by the regulations in force.

The amount of selenium in the composition used according to the present invention ranges from 0.0005 to 0.05%, preferably from 0.001 to 0.01% by weight with respect to the total weight of said composition.

Advantageously, the selenium content in the composition corresponds to the maximum content authorized by the regulations in force.

Advantageously, the composition used according to the invention comprises vitamin E.

Preferably, the vitamin E is used in the composition according to the invention in a cystine/vitamin E ratio of from 30 to 36, preferably from 32 to 34.

Preferably, the amount of vitamin E in the composition used according to the invention ranges from 0.5 to 10%, preferably from 1 to 4% by weight based on the total weight of said composition.

Advantageously, the composition used according to the invention comprises horsetail extract.

Preferably, the amount of horsetail extract in the composition used according to the invention ranges from 0.1 to 2%, preferably from 0.5 to 1.5% by weight based on the total weight of said composition.

Advantageously, the composition used according to the invention does not comprise gooseberry extract.

Advantageously, the composition used according to the invention comprises a melon juice extract.

Preferably, the amount of melon juice extract in the composition used according to the invention ranges from 0.5 to 2.5%, preferably from 1 to 2% by weight based on the total weight of said composition.

Advantageously, the composition used according to the invention does not comprise mandarin extract.

According to a particular mode of the invention, the composition used according to the invention does not comprise tyrosinase inhibiting plant extracts.

According to another particular mode of the invention, the composition used according to the invention does not comprise at least one plant extract selected from the following plant extracts: extracts of arbutus, bearberry, lingonberry, callune vulgaris, ericaceae, rosaceae, saxifragaceae, liquorice, Japanese mulberry, artichoke, yarrow, matricaria, skullcap, grape, cranberry, maritime pine, grape seed, angelica, polypodean fern, tea, sugar cane, apple, rowan, grape, citrus, chestnut, false pepper, pomegranate, strawberry, geranium, intermediate chickweed, sea buckthorn, honeysuckle, blackcurrant, evening primrose, oregano, thyme, ginseng, kudzu, corn, aloe, blackberry, blueberry, chicory, mushroom extracts and extracts of "Rainbow" brown algae.

Advantageously, the composition is prepared by mixing the various components in the form of powders.

Advantageously, the composition used in accordance with the invention may additionally comprise a physiologically acceptable vehicle, suitable for oral use, such as in particular an aqueous phase.

The composition used in accordance with the invention may be formulated with the excipients usually used in compositions intended for oral administration, in particular humectants, thickeners, texturing agents, flavouring agents, coating agents, preservatives, antioxidants, colourings, plant extracts.

Of course, the person skilled in the art will take care to choose these excipients so as not to alter the properties of the said composition.

The composition used in accordance with the invention may be formulated according to one of the following presentations: a capsule, a dragée, a tablet, a soft or hard capsule, or a beverage, a suspension, a solution or a gel.

The formulation of the said composition in accordance with the invention involves conventional processes which are part of the general skills of the person skilled in the art.

The composition according to the present invention can be obtained by mixing the various components of the composition in the required ratios and/or amounts.

The present invention is further directed to a process for preparing the composition used according to the invention comprising the following steps:
- have cystine;
- have glutathione;
- have glycine;
- have glutamine;
- have calcium ascorbate;
- optionally have at least one component selected from the group consisting of zinc or one of its salts, copper or one of its salts, selenium or one of its salts, vitamins B, in particular B3, B5, B6 and/or B8, vitamin E, melon juice extracts and horsetail extracts, and mixtures of these components
- carry out the mixing of cystine, glutathione, glycine, glutamine, calcium ascorbate and at least one possible other component.

As already mentioned, the present invention is intended for cosmetic use, by the oral route, of a composition as active ingredient for whitening and/or lightening the skin and/or depigmenting the skin and in particular for reducing the size of pigmentary brown spots, the said composition comprising at least cystine and glutathione in a cystine/glutathione ratio ranging from 1.5 to 4.

The use of the composition according to the invention does not belong to the therapeutic field. It is a nutraceutical, non-therapeutic composition.

Said use can also be described as a dietary supplement dedicated to whitening and/or lightening the skin and/or depigmenting the skin, in particular to reduce the size, attenuate or even remove brown pigmentation spots, or prevent, reduce and/or treat an alteration of the skin tone. More particularly, the said use makes it possible to reduce, attenuate and eliminate skin pigmentation defects such as melasma or pregnancy mask, and lentigos, particularly senile lentigos.

The cosmetic treatment method according to the invention is also intended to prevent and/or treat the signs of skin ageing, in particular senescence spots.

There are various methods of assessing skin colour in vivo including instrumental and visual assessment methods. Instrumental, more objective evaluation methods are preferred, particularly on the grounds that the effects of lightening/whitening/depigmenting products are slow to take effect.

In the cosmetic field, a commonly used method to assess skin color is the measurement of L*a*b* values by spectrophotometry.

The system classically used to evaluate the colour is the CIELab system in which the following parameters are defined:
- L*, the lightness derived from the luminance of the surface, defines the axis from black/dark (0) to white/light (100),
- a* defines the axis from green (−100) to red (+100),
- b* defines the axis from blue (−100) to yellow (+100).

The L* parameter is a good marker for assessing skin lightening/whitening: the lighter the skin, the higher the L* value.

Generally, a variation of the L* parameter of the order of 1% is a significant result. Nevertheless the best description of lightening/whitening is given by combining the parameters L* and b* to define the Individual Typology Angle (ITA) 'Petit L., Pierard G E, Skin lightening products revisited, International Journal of Cosmetic Science, 2003; 25. 169.-181."

The ITA is calculated using the formula:

$$ITA = \mathrm{ArcTan}[(L^* - 50)/b^*] \times (180/\pi)$$

A change in ITA of about 5% is a significant result.

The evaluation of the pigmentary brown spots, in particular the evolution of their surface (in mm2), is measured by pixelation, for example on the face in the cheek area, by comparing digital photographs with crossed polarization taken at the beginning of the experiment (day 0), at mid-experiment (day 45) and at the end of the experiment (day 90).

The present invention also relates to a non-therapeutic, cosmetic method for whitening and/or lightening and/or depigmenting the skin, in particular for reducing the size of pigmentary brown spots, comprising a step of administering to an individual orally a composition comprising at least cystine and glutathione in a cystine/glutathione ratio ranging from 1.5 to 4, preferably from 1.5 to 3, and preferably from 1.5 to 2.5 and advantageously from 1.8 to 2.2.

In particular the invention is directed to a method according to the invention in which the following daily doses of active material are administered:
- cystine in an amount of 0.001 to 2 g, preferably 0.1 to 1.0 g and preferably about 0.3 to 0.8 g;
- glutathione in a content of 0.001 to 1 g, preferably 0.05 to 0.5 g and preferably about 0.1 to 0.4 g;
- glycine in an amount of 0.001 to 1 g, preferably 0.005 to 0.5 g and preferably about 0.01 to 0.1 g;
- glutamine in an amount of 0.001 to 1 g, preferably 0.01 to 0.5 g and preferably about 0.05 to 0.2 g,
- calcium ascorbate in an amount of 0.001 to 1 g, preferably 0.01 to 0.5 g and preferably about 0.05 to 0.2 g.

Advantageously, the following daily doses are administered:
- vitamin B3 at a level corresponding to 0.01 to 0.03 g nicotinamide;
- vitamin B5 at a level corresponding to 0.010 to 0.015 g of calcium pantothenate;
- vitamin B6 at a level corresponding to 0.001 to 0.005 g pyridoxine hydrochloride;
- vitamin B8 at a level corresponding to 0.0001 to 0.0005 g biotin;
- zinc or a salt thereof with a zinc content of 0.005 to 0.015 g;
- copper or a salt thereof in a copper content of 0.001 to 0.002 g,
- vitamin E in a content corresponding to a content of 0.005 to 0.1 g;
- concentrated melon juice extract in an amount of 0.005 to 0.015 g
- horsetail extract in an amount of 0.001 to 0.01 g The process according to the invention is generally implemented by daily administration of the composition used according to the present invention or daily doses according to the present invention. This administration can be done as a single daily dose, two daily doses, three daily doses or even four daily doses, for example at mealtimes, or advantageously in two doses, one in the morning and the other in the evening.

The process according to the invention is generally implemented over a period varying from one to several weeks or even several months. This treatment period can be repeated several times during a year.

The following examples are intended to illustrate the invention without limiting its scope.

Examples

I/Compositions

A composition A according to the invention and a comparative composition B, both in capsule form, are prepared.

In table 1, the ingredients of composition A in mg, the percentage by weight of the ingredients in composition A, and the ingredients of composition B in mg are shown respectively.

To prepare compositions A and B, the ingredients are weighed and mixed at room temperature. The compositions A and B prepared in this way are stable and are put into capsules.

TABLE 1

| Ingredients | Composition A according to the invention in mg | of weight in composition A | Comparative composition B in mg |
|---|---|---|---|
| L-Cystine | 250.00 | 40.19 | 250.00 |
| L-Glutathione | 125.00 | 20.10 | — |
| L-Glutamine | 60.00 | 9.65 | 60.00 |
| Glycine | 30.00 | 4.82 | 30.00 |
| Vitamin E a.i. 50% | 15.00 | 2.41 | 15.00 |
| Calcium ascorbate | 55.00 | 8.84 | 55.00 |
| Melon juice concentrate | 10.00 | 1.61 | 10.00 |
| Dry extract of horsetail aerial parts | 5.00 | 0.80 | 5.00 |
| Cu-amino acid chelate a.i. 10% | 7.49 | 1.20 | 7.49 |
| Zn-amino acid chelate a.i. 20% | 24.99 | 4.02 | 24.99 |
| Se-amino acid chelate a.i. 1% | 3.50 | 0.56 | 3.50 |
| Vitamin B3 | 8.91 | 1.43 | 8.91 |
| Vitamin B5 (Calcium Pantothenate) | 6.00 | 0.97 | 6.00 |
| Vitamin B6 (pyridoxine hydrochloride) | 1.05 | 0.17 | 1.05 |
| Vitamin B8 (biotin) | 0.15 | 0.02 | 0.15 |
| Magnesium stearate | 19.91 | 3.20 | 13.92 |
| Maltodextrin | — | — | 130.99 |
| Capsule | 118.00 | 0 | 118 |
| Total ingredients + capsule | 740 | 100 | 740 |

Two other compositions were prepared: the placebo C and the comparative composition D presented below Placebo C The placebo C composition included 622 mg of magnesium stearate in a 118 mg capsule.

Composition D

Composition D comprising the following ingredients shown in Table 2 is prepared by mixing the ingredients at room temperature.

TABLE 2

| Ingredients | Composition A according to the invention in mg | of weight in composition A | Comparative composition B in mg |
|---|---|---|---|
| L-Cystine | 250.00 | 40.19 | 250.00 |
| L-Glutathione | 125.00 | 20.10 | — |
| L-Glutamine | 60.00 | 9.65 | 60.00 |
| Glycine | 30.00 | 4.82 | 30.00 |
| Vitamin E a.i. 50 % | 15.00 | 2.41 | 15.00 |
| Calcium ascorbate | 55.00 | 8.84 | 55.00 |
| Melon juice concentrate | 10.00 | 1.61 | 10.00 |
| Dry extract of horsetail aerial parts | 5.00 | 0.80 | 5.00 |
| Cu-amino acid chelate a.i. 10% | 7.49 | 1.20 | 7.49 |
| Zn-amino acid chelate a.i. 20% | 24.99 | 4.02 | 24.99 |
| Se-amino acid chelate a.i. 1% | 3.50 | 0.56 | 3.50 |
| Vitamin B3 | 8.91 | 1.43 | 8.91 |
| Vitamin B5 (Calcium Pantothenate) | 6.00 | 0.97 | 6.00 |
| Vitamin B6 (pyridoxine hydrochloride) | 1.05 | 0.17 | 1.05 |
| Vitamin B8 (biotin) | 0.15 | 0.02 | 0.15 |
| Magnesium stearate | 19.91 | 3.20 | 13.92 |
| Maltodextrin | — | — | 130.99 |
| Capsule | 118.00 | 0 | 118 |
| Total ingredients + capsule | 740 | 100 | 740 |

II/Measurements of the Activity of the Compositions

The daily amounts shown in Table 3 were administered to each subject for 90 days.

TABLE 3

| | L-Cystine in mg | L-Glutathione in mg | L-Cysteine in mg |
|---|---|---|---|
| Composition A according to the invention (2 capsules per day) | 500 | 250 | — |
| Composition C Placebo (2 capsules per day) | — | — | — |
| Comparative composition B (2 capsules per day) | 500 | — | — |
| Comparative composition D (1 capsule per day) | — | 250 | 100 |

The study was conducted on 120 subjects, double-blind, randomized: 30 subjects were given composition A, 30 subjects were given composition B, 30 subjects were given composition C and 30 subjects were given composition D.

The compositions were administered for 90 days.

Topics

The subjects selected met the following criteria:

healthy subjects, age between 30 and 50 years, light skin corresponding to phototypes III and IV on the Fitzpatrick scale and presenting one or more brown spots on the face, i.e. at least one spot whose smallest dimension was at least 2.5 mm in diameter.

Skin colour was assessed spectrophotometrically using a CM 700D spectrophotometer/colourimeter (Konica-Minolta) by measuring the L*a*b* values and calculating the Individual Typology Angle (ITA) value.

The L* parameters of the ITA are used to measure the whitening/lightening of the skin.

Assessment of brown spot reduction was performed by measuring spot size on cross-polarized digital photographs.

Measurements were taken at D=0, D 45 (after 45 days of treatment) and D 90 (after 90 days of treatment).

Table 4 presents the evolution of each criterion (in %) compared to the beginning of the study at D0 and for each composition.

TABLE 4

|  | Composition A (2 capsules per day) | Placebo C (2 capsules per day) | Composition comp. B (2 capsules per day) | Composition comp. D (1 capsule per day) |
|---|---|---|---|---|
| Brown spot size[1] at D 45 | −16.2%*^ | +4.3% | +1.4% | −4.4% |
| Brown spot size[1] at D 90 | −34.4%*^ | +4.4% | +4.8% | −3.6% |
| ITA measured on the cheek[2] at D 45 | +2.2% | −3.5% | −1.8% | −1.0% |
| ITA measured on the cheek[2] at D 90 | +8.7%*^ | +0.5% | −0.8% | −1.0% |
| L*measured on the cheek[3] at D 45 | +0.6% | −0.1% | −0.1% | +0.3% |
| L* measured on the cheek[3] at D 90 | +1.8%*^ | +0.4% | −0.1% | +0.1% |
| ITA measured on the wrist[2] at D 45 | +5.1%* | −2.6% | −2.0% | −1.1% |
| ITA measured on the wrist[2] at D 90 | +6.7%* | −0.7% | +3.9% | +2.0% |
| L*measured on the wrist[3] at D 45 | +0.8% | −0.4% | −0.5% | −0.3% |
| L* measured on the wrist[3] at D 90 | +1.1%* | −0.1% | +0.4% | 0.0% |

[1]measurement of the evolution in % of the surface (mm2) of the brown spots,
[2]measurement of the evolution of the individual typology angle ITA,
[3]measurement of the evolution of the clarity L*,
*statistically significant change compared to D0,
^the variations observed with composition A are significantly different from those observed with the 3 other compositions.

The composition according to the invention allows a significant reduction in the size of brown spots (−16.2% at 45 days and −34.4% at 90 days), part of the spots are no longer visible, the skin appears more even.

It also allows an increase in skin lightening/whitening measured by an increase in the L* parameter on both the cheek (+0.6% at 45 days and +1.8% at 90 days), and the wrist (+0.8% at 45 days and +1.1% at 90 days), and a significant increase in the ATI° on both the cheek (+2.2% at 45 days and +8.7% at 90 days) and the wrist (+5.1% at 45 days and +6.7% at 90 days)

The proportion of subjects showing a reduction in the surface area of brown spots at 90 days is 87% with composition A according to the invention, this value is high and significantly different from those obtained with the placebo composition C (40%), with composition B (50%) and with composition D (39%).

Similarly, the proportion of subjects showing skin lightening/whitening at 90 days with an increase in the ITA value on the cheek is 77%, which is significantly higher than those of the placebo composition C (43%), B (47%) and D (39%).

There is also a whitening/lightening effect on brown spots.

The invention claimed is:

1. A non-therapeutic, cosmetic, oral composition for whitening and/or lightening the skin and/or depigmenting the skin, comprising at least cystine and glutathione in a cystine/glutathione ratio of 3, wherein the cystine is present in an amount from 30 to 60% by weight based on the total weight of said composition, wherein the glutathione is present from 10 to 30% by weight based on the total weight of said composition, and wherein the composition does not comprise gooseberry extract.

2. The composition according to claim 1, wherein the cystine comprises less than 5 ppm of heavy metals.

3. The composition according to claim 1, wherein the composition comprises glycine in a cystine/glycine ratio of from 7 to 9.5.

4. The composition according to claim 1, wherein the composition comprises glutamine in a cystine/glutamine ratio of from 3.5 to 5.0.

5. The composition according to claim 1, wherein the composition comprises calcium ascorbate in a cystine to calcium ascorbate ratio of from 3.5 to 5.5.

6. The composition according to claim 1, wherein the composition comprises at least one component selected from the group consisting of zinc or one of its salts, copper or one of its salts, selenium or one of its salts, one or more B vitamins, vitamin E, melon juice extracts, horsetail extracts and mixtures thereof.

7. The composition according to claim 1, wherein the composition comprises glycine in a cystine/glycine ratio of from 7 to 9.5, glutamine in a cystine/glutamine ratio of from 3.5 to 5.0, and calcium ascorbate in a cystine to calcium ascorbate ratio of from 3.5 to 5.5.

8. A method of preparing the composition according to claim 7, comprising the following steps:
   providing cystine;
   providing glutathione;
   providing glycine;
   providing glutamine;
   providing calcium ascorbate;
   optionally providing at least one component selected from the group consisting of zinc or one of its salts, copper or one of its salts, selenium or one of its salts, B vitamins, vitamin E, melon juice extracts, horsetail extracts, and mixtures thereof;
   wherein the cystine and glutathione are present in a cystine/glutathione ratio of 3, wherein the cystine is present in an amount from 30 to 60% by weight based on the total weight of said composition, wherein the glutathione is present from 10 to 30% by weight based on the total weight of said composition, and wherein the composition does not comprise gooseberry extract;
   and mixing the cystine, the glutathione, the glycine, the glutamine, the calcium ascorbate and, optionally, the at least one component.

9. A non-therapeutic, cosmetic method for whitening and/or lightening and/or depigmenting the skin, comprising a step of administering to an individual orally a non-therapeutic, cosmetic, oral composition for whitening and/or lightening the skin and/or depigmenting the skin, comprising at least cystine and glutathione in a cystine/glutathione ratio of 3, wherein the cystine is present in an amount from 30 to 60% by weight based on the total weight of said composition, wherein the glutathione is present from 10 to 30% by weight based on the total weight of said composition, and wherein the composition does not comprise gooseberry extract.

10. The method according to claim 9, wherein, the following daily doses of active material are administered: cystine in a content ranging from 0.001 to 2 g; glutathione in a content ranging from 0.001 to 1 g; glycine in a content ranging from 0.001 to 1 g; glutamine in an amount of 0.001 to 1 g; and calcium ascorbate in an amount of 0.001 to 1 g.

11. The method according to claim 9, wherein the following daily doses are administered:

vitamin B3 in a content corresponding to a content ranging from 0.01 to 0.03 g of nicotinamide;

vitamin B5 in a content corresponding to a content ranging from 0.010 to 0.015 g of calcium pantothenate;

vitamin B6 in a content corresponding to a content ranging from 0.001 to 0.005 g of pyridoxine hydrochloride;

vitamin B8 in a content corresponding to a content ranging from 0.0001 to 0.0005 g of biotin;

zinc or a salt thereof in a zinc content of from 0.005 to 0.015 g; copper or a salt thereof in a copper content of from 0.001 to 0.002 g;

vitamin E in a content corresponding to a content of from 0.005 to 0.1 g; melon juice extract in a content of from 0.005 to 0.015 g; and horsetail extract in a content of from 0.001 to 0.01 g.

12. A non-therapeutic, cosmetic method according to claim 9, for reducing the size of pigmentary brown spots.

\* \* \* \* \*